United States Patent
Pisharodi

(12)
(10) Patent No.: US 6,355,038 B1
(45) Date of Patent: *Mar. 12, 2002

(54) MULTI-AXIS INTERNAL SPINAL FIXATION

(75) Inventor: Madhavan Pisharodi, Brownsville, TX (US)

(73) Assignee: Perumala Corporation (KY)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/161,141

(22) Filed: Sep. 25, 1998

(51) Int. Cl.[7] .............................................. A61B 17/58
(52) U.S. Cl. ............................ 606/61; 606/72; 411/538
(58) Field of Search ............................ 606/61, 65, 66, 606/72, 73; 411/538, 546, 537

(56) References Cited

U.S. PATENT DOCUMENTS

| | | | |
|---|---|---|---|
| 4,696,290 A | | 9/1987 | Steffee |
| 5,047,029 A | * | 9/1991 | Aebi et al. ..................... 606/61 |
| 5,092,893 A | | 3/1992 | Smith |
| 5,129,899 A | | 7/1992 | Small et al. |
| 5,201,734 A | * | 4/1993 | Cozad et al. .................. 606/62 |
| 5,312,404 A | * | 5/1994 | Asher et al. ................... 606/61 |
| 5,344,421 A | | 9/1994 | Crook |
| 5,531,747 A | | 7/1996 | Ray |
| 5,578,035 A | * | 11/1996 | Lin ............................. 606/68 |
| 5,716,357 A | * | 2/1998 | Rogozinski ................... 606/61 |
| 5,743,907 A | | 4/1998 | Asher et al. |
| 5,906,466 A | * | 5/1999 | Eandi .......................... 411/538 |

FOREIGN PATENT DOCUMENTS

| | | |
|---|---|---|
| EP | 0846444 | 6/1998 |
| FR | 2683445 | 5/1993 |
| FR | 2697993 | 5/1994 |
| FR | 2735011 | 12/1996 |

OTHER PUBLICATIONS

Smith & Nephew Spine brochure, Simmons Plating System—Kambin Offset Bolt (Smith & Nephew Spine, a Division of Smith & Nephew Richards Inc., Memphis, TN), Date Unknown,.

(List continued on next page.)

*Primary Examiner*—David O. Reip
*Assistant Examiner*—Julian W. Woo
(74) *Attorney, Agent, or Firm*—Mark R. Wisner

(57) ABSTRACT

A multi-axis correction washer for use with a spinal stabilizer for internal spinal fixation. The bodies of the washer are provided in cylindrical and wedge-shaped cylindrical configurations with a hole in the center of the longitudinal axis of the cylinder and/or offset from the center axis of the cylindrical washer and a shoulder or other structure for rotatably engaging a hole in a spinal implant. The spinal implant can be a plate and screw-type, ladder-type, or monorail-type spinal fixation system. The washer is rotated to provide an infinite range of angles and screw placements relative to the central axis of the spinal column for maximum flexibility of installation and to effectively transfer the load on the spinal column to the implant, all while maintaining an angle of approximately 90° between the head of the screw and/or nut and the washer which engages the implant.

10 Claims, 6 Drawing Sheets

OTHER PUBLICATIONS

Moss Miami Titanium brochure (Depuy Motech, Warsaw, IN, 1996).

Dynalok Anterior Fixation System brochure (Danek Medical, Inc., Memphis, TN, Apr. 1993).

Versalok Low Back Fixation System brochure (Wright Medical Technology, Arlington, TN, 1996).

Simmons Plating System Catalog, Surgical Technique (Smith & Nephew Spine, a Division of Smith & Nephew Richards Inc., Memphis, TN, Oct. 1993).

Rogozinski, C., et al., The Rogozinski Spinal Rod System: A New Internal Fixation of the Spine, in D.M. Arnold, et al. (Eds.), Spine: Pedicle Fixation of the Lumbar Spine, Hanley & Belfus, Inc., Philadelphia, pp. 107–120 (1992).

Krag, M.H., Vermont Spinal Fixator, in D.M. Arnold, et al. (Eds.), Spine: Pedicle Fixation of the Lumbar Spine, Hanley & Belfus, Inc., Philadelphia, pp. 120–145 (1992).

Brantigan, J.W., et al., Posterior Lumbar Interbody Fusion Technique Using the Variable Screw Placement Spinal Fixation System, in D.M. Arnold, et al. (Eds.), Spine: Pedicle Fixation of the Lumbar Spine, Hanley & Belfus, Inc., Philadelphia, pp. 175–200 (1992).

Heim, S.E., et al., Danek Plate and Screw System, in D.M. Arnold, et al. (Eds.), Spine: Pedicle Fixation of the Lumbar Spine, Hanley & Belfus, Inc., Philadelphia, pp. 210–234 (1992).

Edwards, C.C., The Edwards Modular System for Three–Dimensional Control of Lumbar Spine, in D.M. Arnold, et al. (Eds.), Spine: Pedicle Fixation of the Lumbar Spine, Hanley & Belfus, Inc., Philadelphia, pp. 235–263 (1992).

An, H.S. and J.M. Cotler (eds.), Spinal Instrumentation, Williams & Wilkins, Baltimore, MD, pp. 197–217, 399–400, 435–456 (1992).

Kostuik, J.P., Anterior Kostuik–Harrington Distraction Systems for the Treatment of Acute and Chronic Kyphotic Deformities, in R.G. Fessler and R.W. Haid, Eds., Current Techniques in Spinal Stabilization, pp. 171–192 (1996).

Fessler, R.G., et al., Utilization of the Texas Scottish Rite Hospital Universal System for Stabilization of the Thoracic and Lumbar Spine, in R.G. Fessler and R.W. Haid, Eds., Current Techniques in Spinal Stabilization, pp. 273–285 (1996).

Gillet, P., Utilization of the Compact Cotrel–Dubousset System for Stabilization of the Thoracolumbar and Lumbar Spine, in R.G. Fessler and R.W. Haid, Eds., Current Techniques in Spinal Stabilization, pp. 297–308 (1996).

Simmons, J.W., Utilization of the Simmons Plating System for Stabilization of the Spine, in R.G. Fessler and R.W. Haid, Eds., Current Techniques in Spinal Stabilization, pp. 325–332 (1996).

Rengachary, S.S., et al., Segmental Fixation of the Lumbosacral Spine Using the Isola/VSP System, in R.G. Fessler and R.W. Haid, Eds., Current Techniques in Spinal Stabilization, pp. 367–378 (1996).

\* cited by examiner

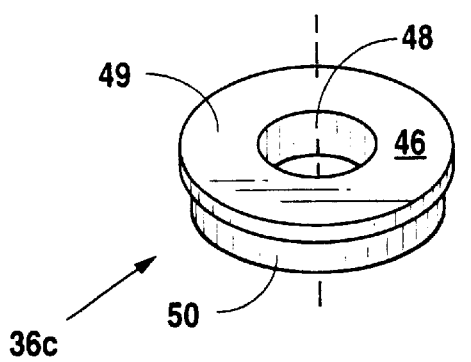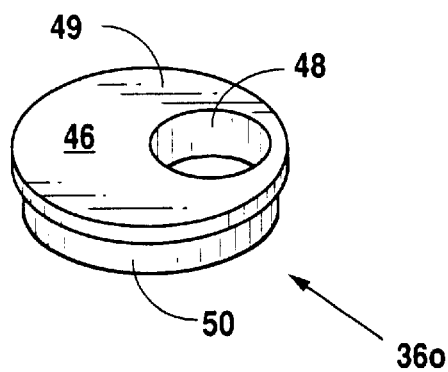
Fig. 4　　　　Fig. 5
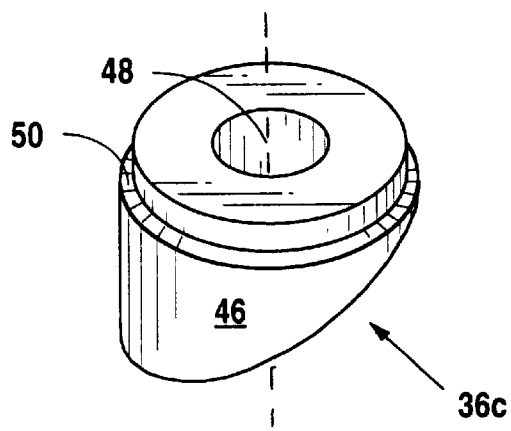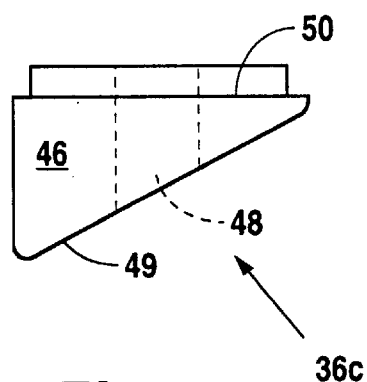
Fig. 6　　　　Fig. 7
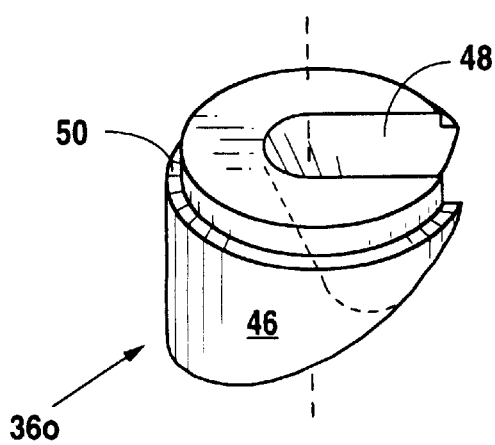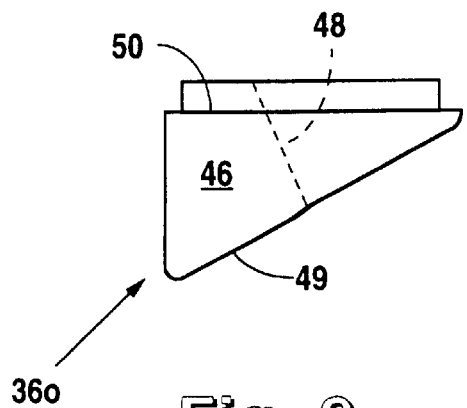
Fig. 8　　　　Fig. 9

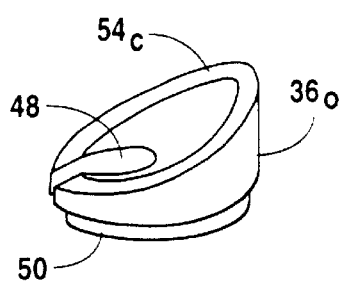
Fig. 10
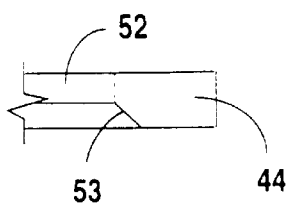
Fig. 13
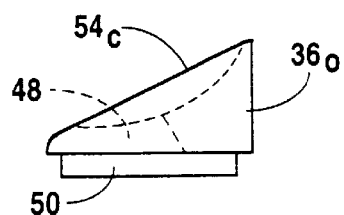
Fig. 11
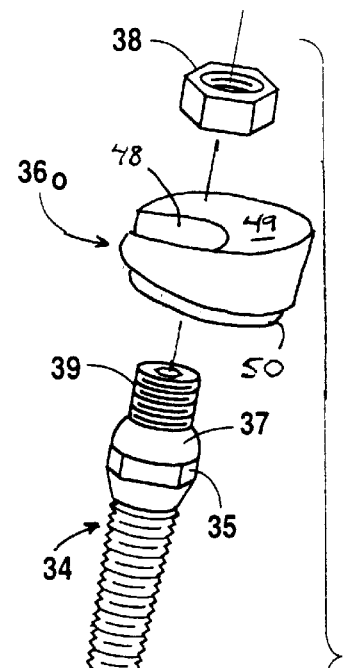
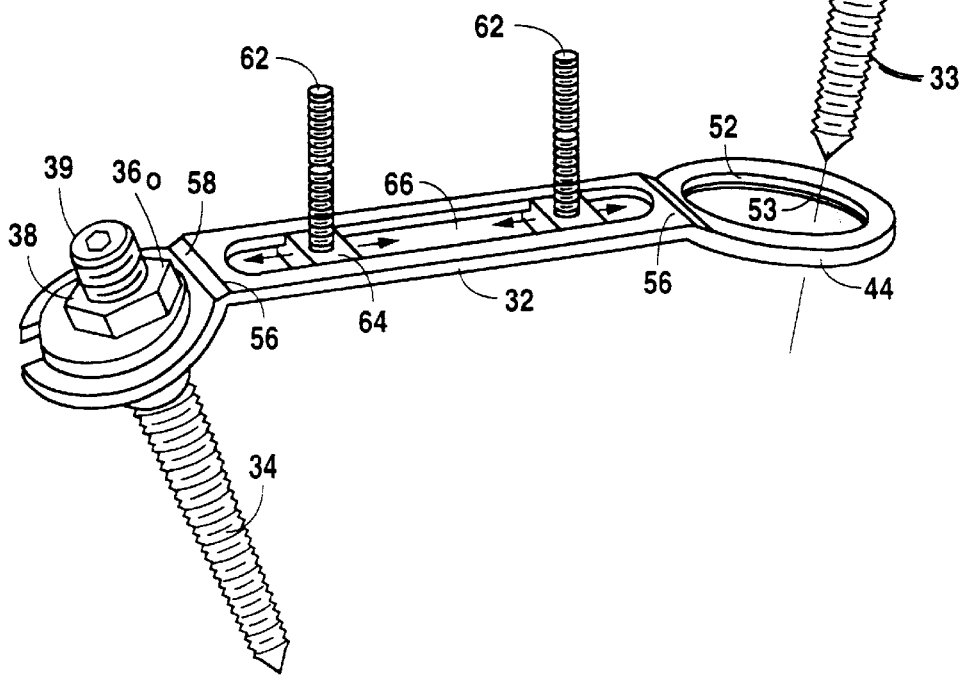
Fig. 12

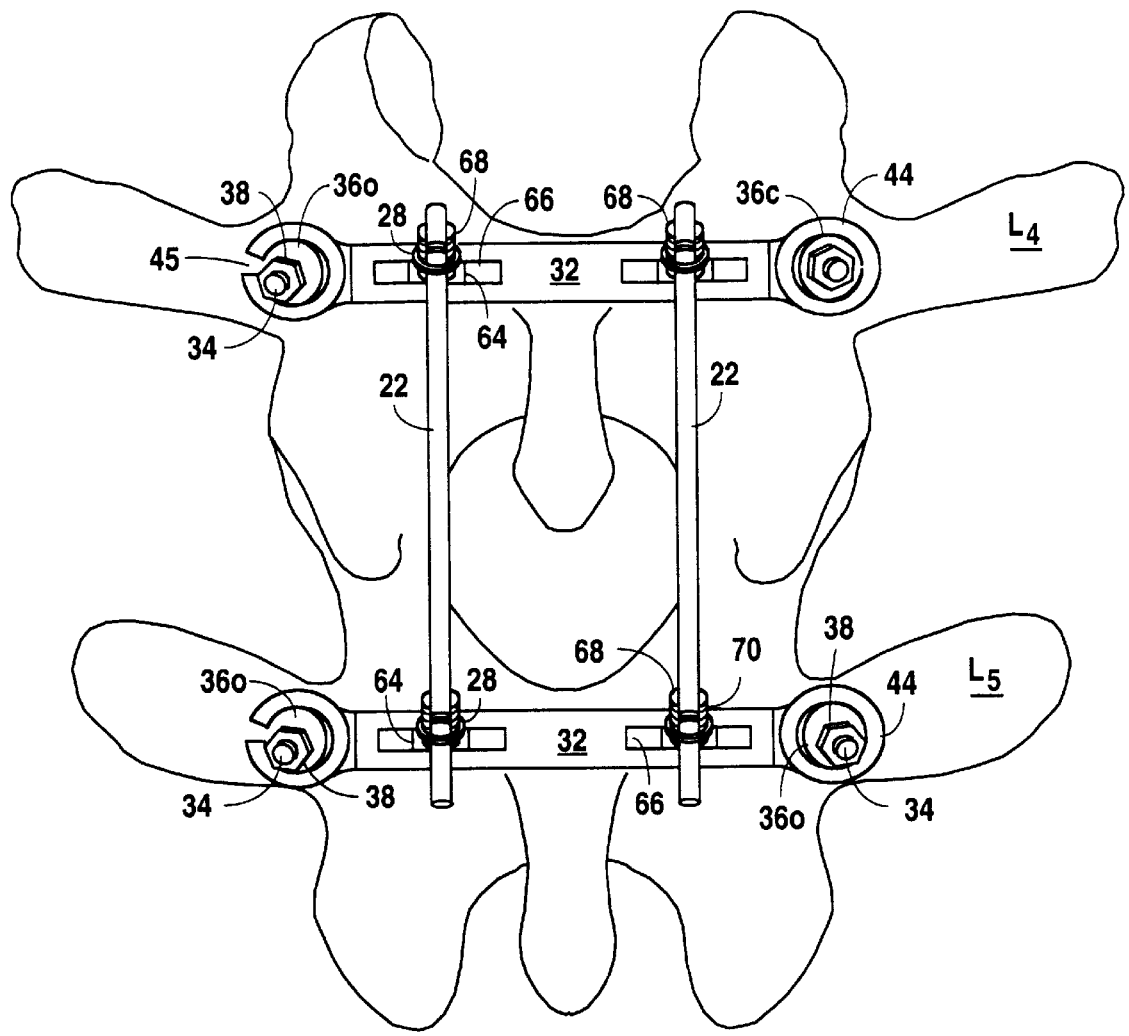
Fig. 14
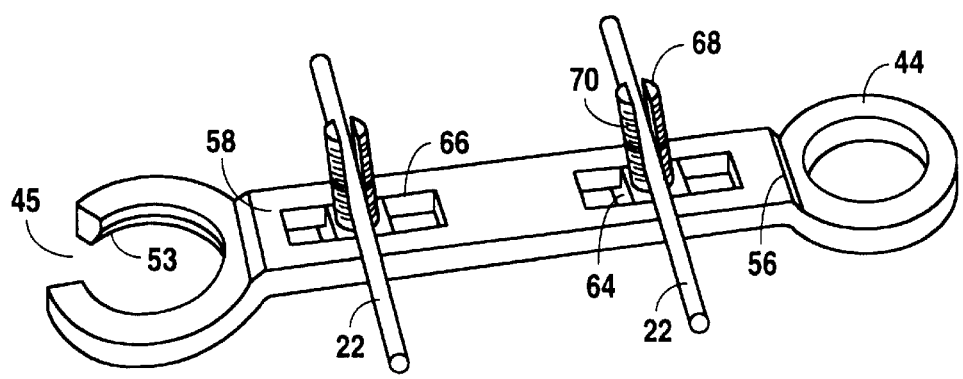

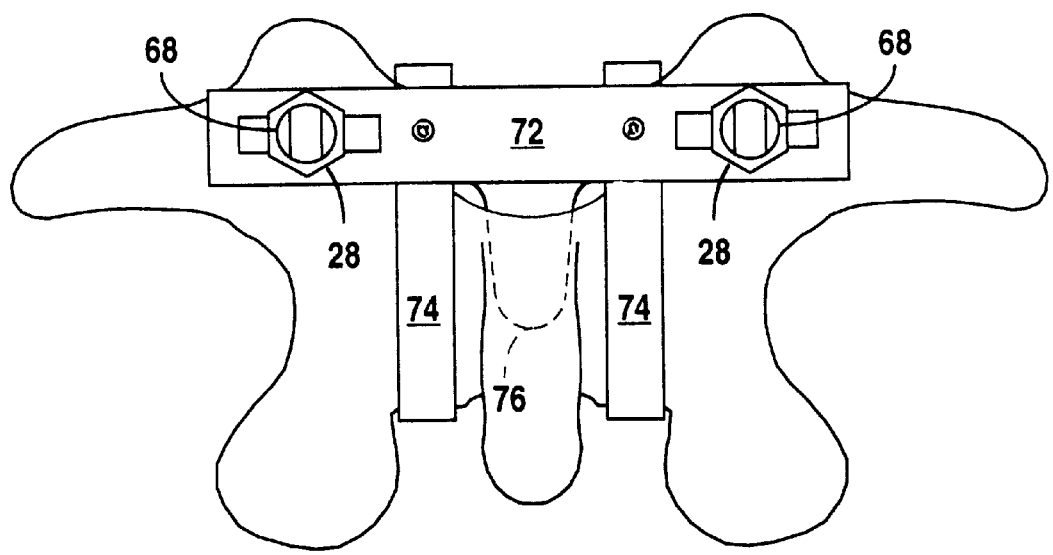
Fig. 16
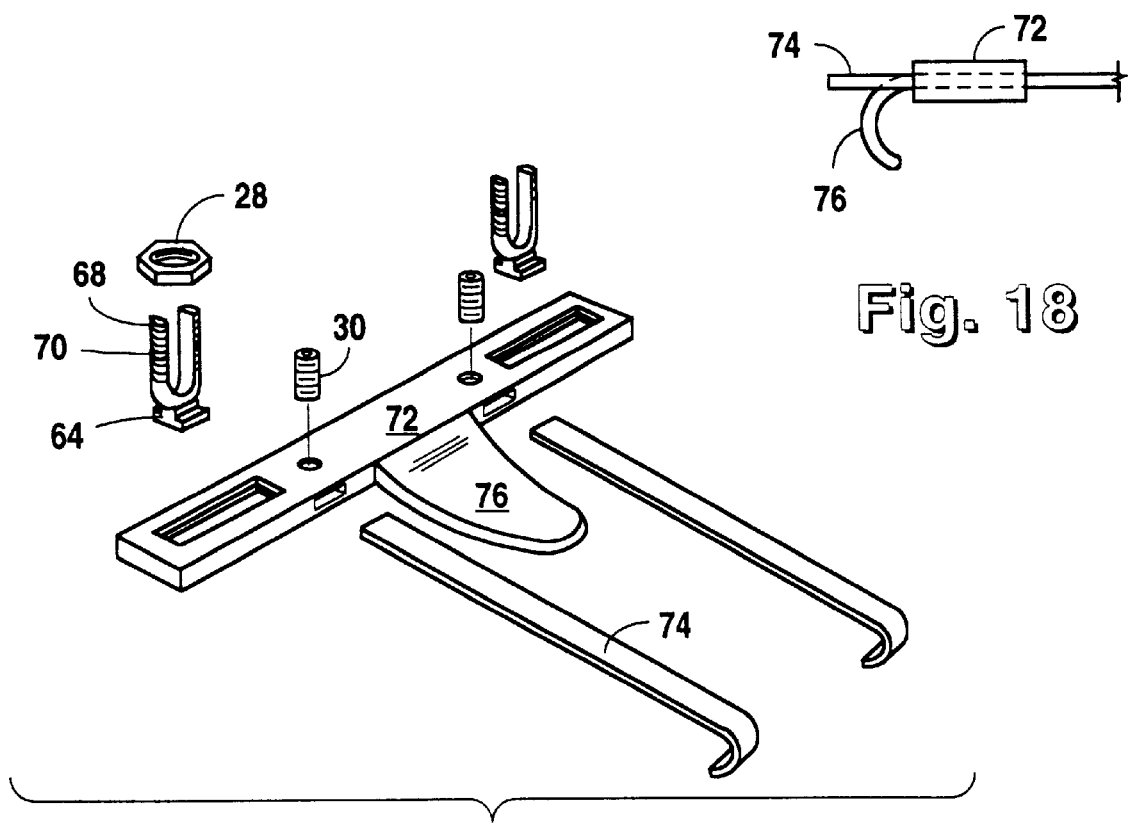
Fig. 18
Fig. 17

MULTI-AXIS INTERNAL SPINAL FIXATION

BACKGROUND OF THE INVENTION

The present invention relates to multi-axis internal spinal fixation. In more detail, the present invention relates to an internal spinal fixation system, and a method of stabilizing, or fixing, the spine for use with either bilateral rods or plates such as the Steffee/variable screw placement system or a central rod and plurality of cross-bars or plates such as the so-called Tacoma Monorail System, utilizing wedge-shaped and/or flat washers having off-set and/or centered openings therein to provide multiple axes for the pedicle screws used to fix the rods, cross-bars, and/or plates to the vertebrae of the patient.

There are many systems available for internal fixation of the spine. Such systems are described in the patent literature (see, for instance, U.S. Pat. Nos. 4,696,290, 5,092,866, and 5,129,899) and the scientific literature (see, for instance, D. M. Arnold and J. E. Lonstein (Eds.), 6 State of the Art Reviews—Spine: Pedicle Fixation of the Lumbar Spine (Philadelphia: Nanley & Belfus, Inc.) 1992 and H. S. An and J. M. Cotler (Eds.), Spinal Instrumentation (Baltimore: Williams & Wilkins) 1992), and are available from such vendors as AcroMed, Smith & Nephew, MOSS® Miami, Osteonics, Sofamor Danek, and others.

A problem with all such systems, however, is the joint between the screws used to affix the system to the pedicle and the rods, cross-bars, and/or plates of the system. As stated in J. M. Cotler, et al., Principles, Indications, and Complications of Spinal Instrumentation: A Summary Chapter, in H. S. An and J. M. Cotler, Spinal Instrumentation pp. 435–456 (Baltimore: Williams & Wilkins) 1992, "[a] significant problem in pedicular screw fixation appears to be at the site of linkage between the screw and rod or plate."

It appears that the problems at the site of this linkage may result from the geometry of the joint between the screw and the rod or plate. This difficult geometry results from several factors, including the different angles and placement of the vertebrae and their relative sizes, the shape of the vertebrae and the spacing between vertebrae, the placement of the screws, the lordosis of the spine, and the need to insert the screws into each vertebra at an angle. With regard to the angle of the pedicle screws, pedicle screws are angled inwardly and upwardly into the vertebra for maximum strength and, because the surfaces of the pedicles of each vertebrae are angled relative to each other, the screws rarely line up across the vertebral body into which they are screwed. Nor do they line up from one vertebra to the adjacent vertebra even if the adjacent vertebrae are the same size and shape (which they generally are not). For a more complete discussion of the biomechanics of the bone-implant interface, reference is made to H. A. Pool and R. W. Gaines, Biomechanics of Transpedicular Screw Spinal Implant Systems, in D. M. Arnold and J. E. Lonstein (Eds.), 6 State of the Art Reviews—Spine: Pedicle Fixation of the Lumbar Spine 37–44 (Philadelphia: Nanley & Belfus, Inc.) 1992, M. R. Pinto, Complication of Pedicle Screw Fixation, in D. M. Arnold and J. E. Lonstein (Eds.), 6 State of the Art Reviews—Spine: Pedicle Fixation of the Lumbar Spine 45–54 (Philadelphia: Nanley & Belfus, Inc.) 1992, and M. H. Krag, Vermont Spinal Fixator, in D. M. Arnold and J. E. Lonstein (Eds.), 6 State of the Art Reviews—Spine: Pedicle Fixation of the Lumbar Spine 121–145 (Philadelphia: Nanley & Belfus, Inc.) 1992, which references are incorporated herein in their entirety by these specific references thereto. Because the pedicle screws do not line up, the rod which runs along the longitudinal axis of the patient's spinal column, which provides the structural rigidity required to stabilize the spine, must either be bent to the location of each screw head or the stabilizer must be provided with adjustable structure which enables the screw head to be attached to the rod.

As a result of this difficulty, the literature includes comments such as the following statement in R. M. Puno and J. A. Byrd III, Transpedicular Screw/Rod Fixation Using the Puno-Winter-Byrd(PWB) System, in D. M. Arnold and J. E. Lonstein (Eds.), 6 State of the Art Reviews—Spine: Pedicle Fixation of the Lumbar Spine 83–106 (Philadelphia: Nanley & Belfus, Inc.) 1992:

"Transpedicular fixation has been proved to be of value in the treatment of spinal disorders . . . However, experience has shown that this method of instrumentation places great demand on the surgeon's skill because of the anatomic constraints related mainly to the anatomy and morphometry of the spinal pedicle."

Many of the above-listed systems, and many of the systems described in the literature, attempt to relieve this burden on the surgeon by providing angled screws (for instance, the AMSET® R-F reduction-fixation system), so-called polyaxial screws (for example, the MOSS® Miami system noted above), full-length, scalloped, open-slot plate design with an undersurface complementary to the shape of the screw head (the Sofamor Danek plate and screw system noted above for example) for optimal positioning of the screws and up to 15° medial-lateral and 30° craniocaudal angulation at the screw-plate interface, and infinitely variable couplers (the so-called Rogozinski spinal rod system for example) which are said to allow rotation through a 130° arc to allow screw placement within the pedicle with no requirement to align each screw with the screw in the adjacent vertebrae.

Although these prior systems address these problems, as evidenced by the fact that new systems are introduced by the same vendors which are already marketing the above-listed systems, no currently available system completely solves all the problems presented by the need for optimal screw placement, angulation of the screw, and effective load transfer from spinal column to implant. An ideal system would (a) accomodate optimal screw placement, height, and angulation, (b) accomodate different sizes and shapes of vertebrae, (c) minimize (or not require) bending or other fabrication during surgery, (d) maintain an angle of approximately 90° between the screw head and the plate or cross-bar to which the screw is attached for effective load transfer from spinal column to implant and to minimize the likelihood of slippage and/or gross failure, and (e) be strong enough to provide lasting and rigid fixation of the spine. Those skilled in the art will recognize that this list is not exhaustive, but is instead intended to illustrate some of the desirable characteristics of an ideal internal fixation system. Other design criteria are also important, and some practicioners may consider some criteria so important that they might not even list others.

So far as is known, none of the above-listed internal fixation systems meets these criteria in every patient. The disadvantages and limitations of currently available systems are made clear from reports in the literature of failure rates (failure of the device, not such complications as infection, phlebitis, seroma, neurologic deficit, etc.) as high as 25% (see R. Roy-Camille, et al., 203 Clin. Orthop. 7 (1986)), 11% (see, S. F. Heim and E. R. Luque, Danek Plate and Screw System, in D. M. Arnold and J. E. Lonstein (Eds.), 6 State of the Art Reviews—Spine: Pedicle Fixation of the Lumbar Spine 201–234 (Philadelphia: Nanley & Belfus, Inc.) 1992), 8% (see, R. M. Puno and J. A. Byrd III, Transpedicular Screw/Rod Fixation Using the Puno/Winter/Byrd (PWB) System, supra), and 2–7% D. M. Arnold and L. L. Wiltse, The Wiltse System of Internal Fixation for the Lumbar Spine, in D. M. Arnold and J. E. Lonstein (Eds.), 6 State of the Art Reviews—Spine: Pedicle Fixation of the Lumbar Spine 55–82 (Philadelphia: Nanley & Belfus, Inc.) 1992.

The currently available systems have other limitations. By way of example, so far as is known, no currently available surgically implanted system can predictably treat rotoscoliosis. Further, no currently available system is conveniently used in multiple level surgery. Multiple level surgery is a challenge for the surgeon because of the need to align the pedicle screws in multiple vertebrae while working under the heavy muscles of the back.

There is therefore a need for improvement of such systems, and it is this improvement to which the present invention is directed. In particular, it is an object of the present invention to improve the screw-plate interface in those systems in which the screw is angled and/or spaced at varying intervals. Another object of the present invention is to provide flexibility of placement, angulation, spacing, and screw height for accomodating the pedicle screws of such systems. Another object of the present invention is to provide a system which is universal in the sense that, although comprised of relatively few parts, it will work with pedicle screws and laminar hooks, thereby providing even more flexibility and ease of use. Another object of the present invention is to provide an internal spinal fixation system which avoids surgery under the heavy muscles of the back so that the surgery is simplified and there is more room for fusion of adjacent vertebrae in the lateral gutter. Other objects, and the advantages, of the present invention will be made clear to those skilled in the art by the following description of the preferred embodiments thereof.

SUMMARY OF THE INVENTION

These objects, and other objects to be made clear by the following detailed description of the preferred embodiments of the invention, are met by providing a spinal stabilizer comprising a rod, a screw, a cross-bar having a hole therein, means for attaching the cross-bar to the rod, and a washer. The washer comprises a cylindrical body having one end angled with respect to the side walls of the cylindrical body and a longitudinal passage therethrough for receiving the screw for affixing the cross-bar to the vertebra of a patient. The washer also comprises means for resting on and rotatably engaging the margins of the hole in the cross-bar so that the body is capable of being rotated in the hole in the cross-bar to provide an infinite variety of angles and pedicle screw placements while maintaining an optimal interface between the head of the screw and the washer so as to effectively transfer the load from the spinal column to the cross-bar.

In another aspect, the present invention contemplates a novel washer for use in connection with an internal spinal stabilizer which comprises a wedge-shaped, cylindrical body with a hole through the body which is offset from the center of the longitudinal axis of the washer. The hole receives a screw for affixing an internal spinal stabilizer to the vertebral body of a patient. Means is formed on said body for rotatably engaging the spinal stabilizer to allow the body to rotate around the 360° of the hole to provide infinite variability in the angle and location of the interface between the screw and the plate.

The present invention also provides a method of affixing a spinal stabilizer to the vertebra of a patient, the stabilizer comprising a washer having an off-center passage therethrough, a cross-bar, and a screw, comprising the steps of engaging the cross-bar with the washer, driving the screw into the vertebral body through the passage in the washer, and changing the angle of the screw relative to the vertebral body to which the cross-bar is affixed by rotating the washer relative to the cross-bar.

In a second embodiment of the method of affixing a spinal stabilizer to the vertebra of a patient, the spinal stabilizer comprises a washer having a cylindrical body with one end angled with respect to the side walls of the cylinder and a longitudinal passage therethrough, a cross-bar, and a screw, and the method comprises the steps of engaging the cross-bar with the washer, driving the screw into the vertebral body through the passage in the washer, and changing the angle of the screw relative to the vertebral body to which the cross-bar is affixed by rotating the washer relative to the cross-bar.

BRIEF DESCRIPTION OF THE DRAWINGS

Referring now to the FIG. 1 of the drawings, there is shown a partially schematic, dorsal view of a portion of the human spinal column having a preferred embodiment of a spinal stabilizer constructed in accordance with the teachings of the present invention surgically affixed thereto.

FIG. 4 is top, perspective view of a preferred embodiment of a washer constructed in accordance with the teachings of the present invention.

FIG. 5 is a top, perspective view of a second preferred embodiment of a washer constructed in accordance with the teachings of the present invention.

FIG. 6 is a bottom, perspective view of a third preferred embodiment of a washer constructed in accordance with the teachings of the present invention.

FIG. 7 is a side elevational view of the washer of FIG. 6.

FIG. 8 is a bottom, perspective view of a fourth preferred embodiment of a washer constructed in accordance with the teachings of the present invention.

FIG. 9 is a side elevational view of the washer of FIG. 8.

FIG. 10 is a perspective view of a second embodiment of the washer of FIG. 8.

FIG. 11 is a side elevational view of the washer of FIG. 10.

FIG. 12 is a partially exploded, perspective view of a portion of the spinal stabilizer of FIGS. 1 and 2.

FIG. 13 is a side elevational view of a portion of the cross-bar of FIG. 12.

FIG. 14 is a partially schematic, dorsal view of a portion of the human spinal column having another alternative embodiment of a spinal stabilizer constructed in accordance with the teachings of the present invention surgically affixed thereto.

FIG. 15 is a perspective view of the cross-bar of the spinal stabilizer of FIG. 14.

FIG. 16 is a dorsal view of a single lumbar vertebrae having an alternative embodiment of a cross-bar constructed in accordance with the teachings of the present invention affixed thereto for use in connection with the spinal stabilizer of FIG. 14.

FIG. 17 is an enlarged, top plan view of the cross-bar of FIG. 16.

FIG. 18 is a detailed, side elevational view of a portion of the cross-bar of FIG. 16.

DETAILED DESCRIPTION OF THE INVENTION

Figure 1:
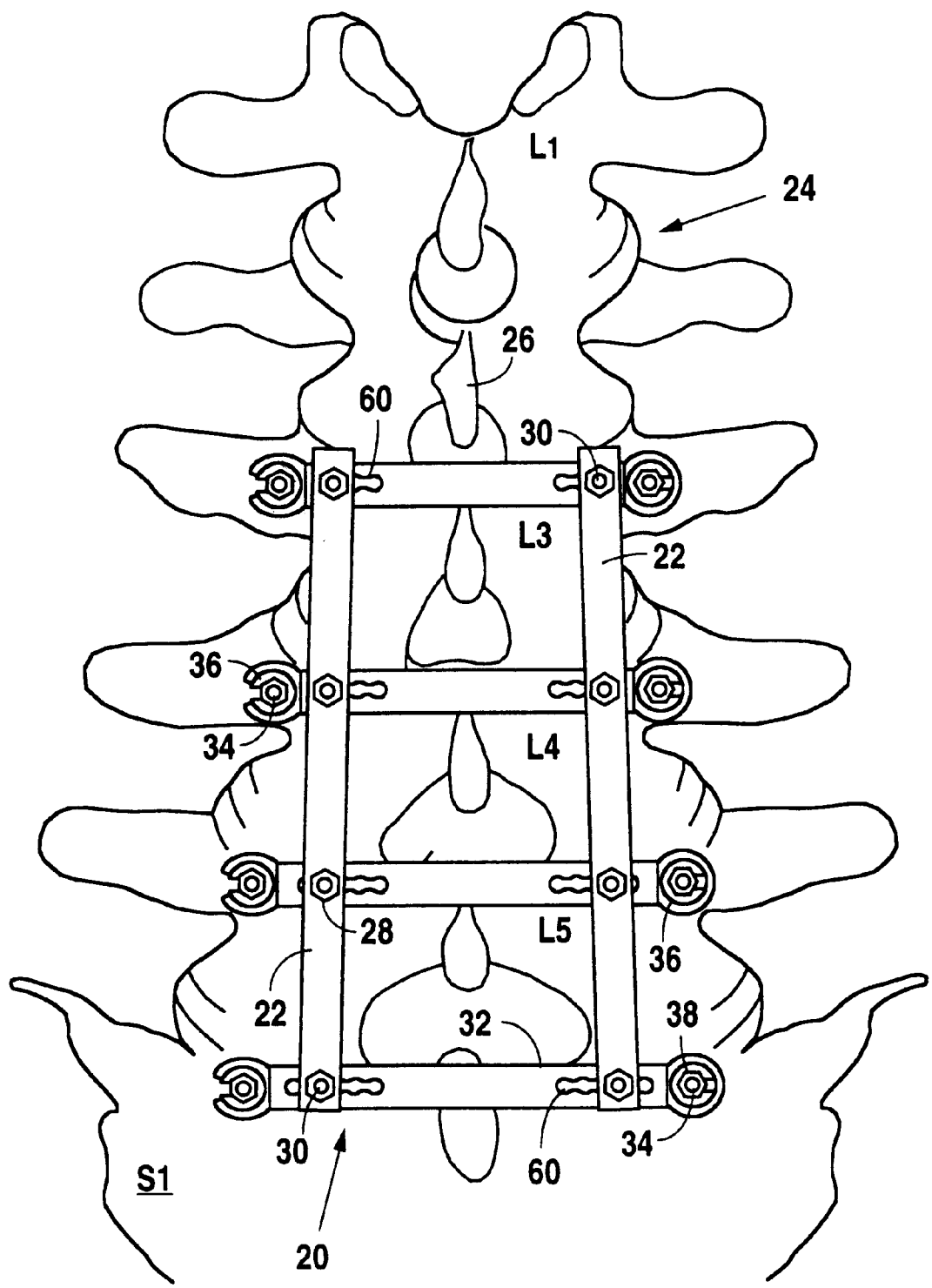
Figure 2:
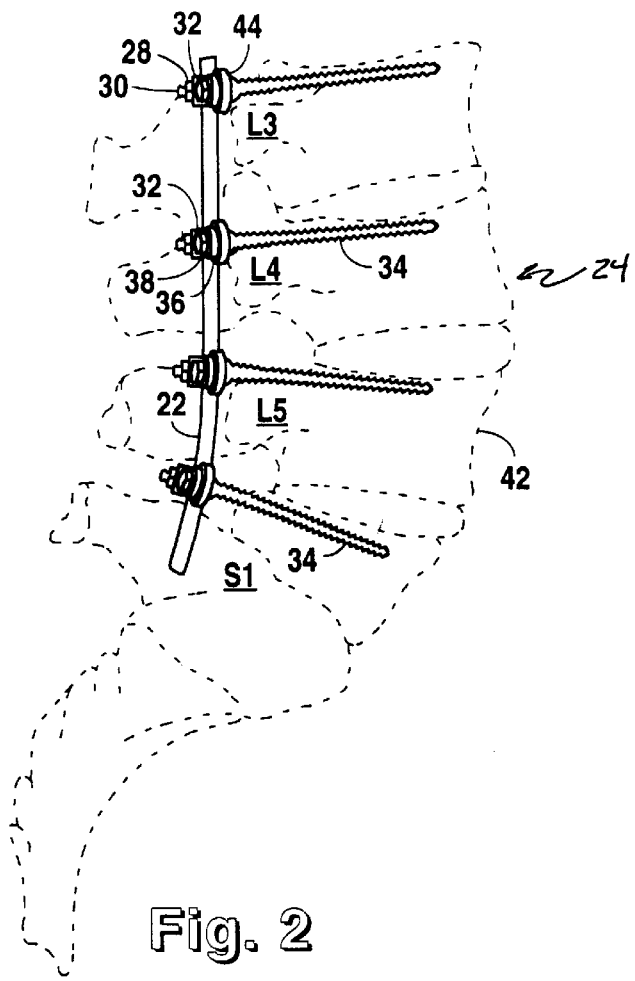
FIG. 2 is a lateral view of the human spinal column having the spinal stabilizer of FIG. 1 affixed thereto and showing the spinal column in phantom lines to show the positions of the pedicle screws used to affix the spinal stabilizer to the spinal column.

A presently preferred embodiment of the spinal stabilizer of the present invention is shown affixed to the spinal column in FIGS. 1 and 2. The preferred embodiment, indicated generally at reference numeral 20, is comprised of two rods 22 oriented along the longitudinal axis of the spinal column 24 on either side of the spinous processes 26 of lumbar vertebrae L3–L5 and the first sacral vertebrae S1. Rods 22 are connected at the level of each vertebrae S1, L3–L5 by nut and screw 28 and 30 to cross-bar, or plate, 32. The screws 30 are preferably of a type known in the art in which the portion of the screw threads projecting through nut 28 is broken off so as not to project any further from the nut 28 than needed. Each cross-bar/plate 32 is affixed to the corresponding vertebrae by a pedicle screw 34, washer 36, and nut 38, screws 34 being anchored in the pedicle 40 (see FIG. 3) of each vertebrae. Screws 34, shown in more detail in FIG. 12, are also of a type known in the art in which the bottom portion 33 is provided with threads for anchoring into the vertebrae, a head 35 with a rounded, or hemispherical upper surface 37, and an upper threaded portion 39 for threadably receiving the nut 38 and the portion of the threads projecting through nut 38 is broken off so as not to project any further through nut 38 than needed. A screw of this type is shown, for instance, in U.S. Pat. No. 5,129,899, which patent is incorporated herein in its entirety by this specific reference thereto.

Figure 3:
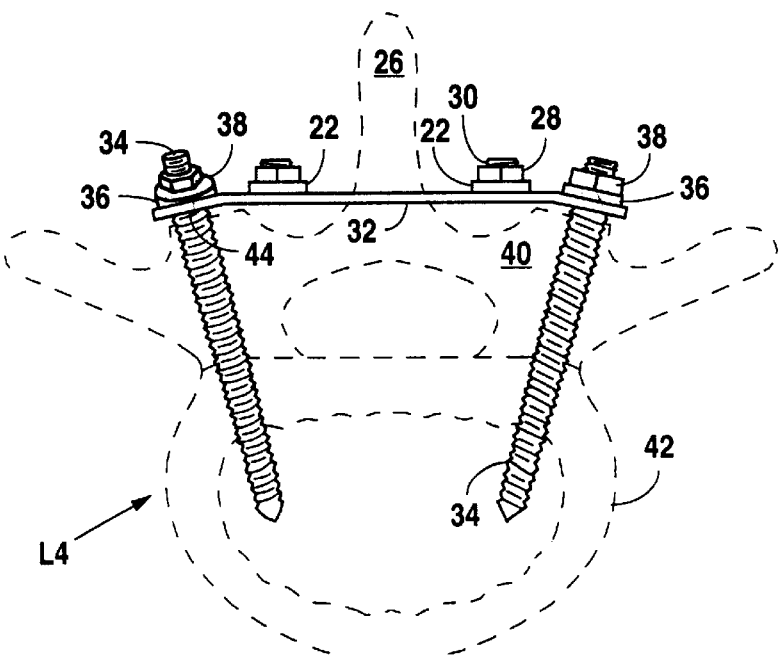
FIG. 3 is a top plan view of a lumbar vertebra having the spinal stabilizer of FIGS. 1 and 2 affixed thereto and showing the vertebra in phantom lines to show the positions of the pedicle screws used to affix the spinal stabilizer to the spinal column.

As noted above, the need for secure anchorage of the screws 34 in the vertebrae, the lordosis of the spine and corresponding curve in rods 22 (best shown in FIG. 2), inward angle of the screws 34 (best shown in FIG. 3), different sizes, spacing, and shapes of the vertebral bodies 42, and many other factors (including the particular pathology which the spinal fixation system is intended to address), require that almost every screw 34 must be oriented at a unique angle relative to rods 22. To illustrate, in FIGS. 1–3, it can be seen that each screw is angled in three axes of a three-dimensional coordinate system (not shown) having its origin on the center axis of the spinal column 24. If the Y coordinate of the coordinate system is coincident with the center of the longitudinal axis of the spinal column 24 (such that+Y is anterior and−Y is posterior), the X coordinate is the lateral dimension, and the Z coordinate is orthogonal to the plane of the paper in FIG. 1 (such that+Z is ventral and−Z is dorsal), it can be seen in FIG. 2 that the positions of the tips of the screws 34 are defined by Y and Z coordinates. Reference to FIG. 3 (in which the Y coordinate of the hypothetical coordinate system runs in and out of the plane of the paper) illustrates that the positions of the tips of the same screws are also defined by an X coordinate.

Referring now to FIG. 3, it can be seen that the ends 44 of cross-bar 32 are angled downwardly, or ventrally (relative to the body of the patient), to accommodate the round shape of the body 42 of the vertebrae L4 to which the cross-bar 32 is affixed by screws 34. Although the cross-bar 32 need not be shaped in this fashion, this bend at the ends 44 of cross-bar 32 serves several advantages other than accommodating the shape of the vertebral body (for instance, reducing the height of the stabilizer in the direction of the Z coordinate of the three-dimensional coordinate system described above) and therefore represents a preferred embodiment of the spinal fixation system of the present invention. However, the downward bends at the ends 44 also introduces yet another angle into the interface between the screw 34 and the cross-bar 32. As a result of the angle of the screw 34 and the bend at the end 44 of cross-bar 32, the longitudinal axis of screw 34 is unlikely to be perpendicular to cross-bar 32 at the interface between the screw 34 and cross-bar 32, and therefore unlikely to optimally transfer load from the spinal column 24 to the spinal stabilizer 20.

FIGS. 4–9 show a plurality of washers 36 constructed in accordance with the teachings of the present invention shaped and/or configured to provide optimal load transfer from the spinal column 24 to the spinal stabilizer 20. The washers $36_c$ and $36_o$ shown in FIGS. 4 and 5, respectively, are comprised of a cylindrical body 46 having a longitudinal passage 48 therethrough for receiving the screw 34 for affixing the spinal stabilizer 20 to the vertebral body 42. The passage 48 through the body 46 of washer $36_c$ is centered on the longitudinal axis (represented by the phantom line in FIG. 4) of washer $36_c$ and the passage 48 in the body 46 of washer $36_o$ (FIG. 5) is offset from the center of the longitudinal axis of the washer $36_o$ for a purpose to be described below. Each of the washers $36_c$ and $36_o$ is also provided with means formed on the body 46 for rotatably engaging the spinal stabilizer 20. In the preferred embodiment shown, the stabilizer engaging means takes the form of a shoulder 50 formed on the body 46 of the washers $36_c$ and $36_o$ which rests on the margins of the hole 52 formed in the ends 44 of cross-bar 32 when the washer $36_c$ or $36_o$ is assembled to the cross-bar 32 in the manner described below.

Those skilled in the art will recognize that the stabilizer engaging means need not be comprised of the shoulder 50. In an alternative embodiment, the stabilizer engaging means takes the form of three or more projections on the surface of the walls of the cylindrical body (the "O.D." of the body) which, when the body is inserted through the hole 52 in the cross-bar 32. create an interference with the margin of hole 52 so that the washer effectively sits in the hole 52 with the projections on the O.D. of the body acting as a spider to support the washer in the hole 52. Alternatively, and particularly in the case of the washers shown in FIGS. 6–10 described below, the O.D. of the body 46 of washer 36 is provided with a groove and the washer is inserted with the angled top surface 49 (see below) up from beneath the hole 52 in cross-bar 32 and rotated so that the groove engages and interacts with the margin of the hole 52 so as to limit the travel of the washer through the hole 52. In another embodiment, the stabilizer engaging means takes the form of a plurality of projections projecting radially inwardly from the margins of the hole in the cross-bar for engaging a shoulder or slot formed on the O.D. of the body of the washer. In yet another embodiment, the washers are comprised of a resilient material such as a medical grade polymeric material which are provided with a groove formed on the O.D. thereof which is press-fit into the hole 52 in cross-bar 32. All such embodiments, and others functioning to allow the washer to rotatably engage the cross-bar which may be developed by those skilled in the art who have the benefit of this disclosure, are considered equivalent to the structure disclosed herein and are therefore considered to be constructed in accordance with the present invention.

Other preferred embodiments of the washer 36 of the present invention are shown in FIGS. 6–7 and 8–9. Again, the hole 48 in the cylindrical body 46 of washer $36_c$ shown in FIGS. 6 and 7 is centered on the longitudinal axis (represented by the phantom line in FIG. 6) of washer $36_c$ and, when viewed from the end 49, the longitudinal passage 48 in the cylindrical body 46 of washer $36_o$ in FIGS. 8 and 9 is offset from the center of the longitudinal axis (represented by the phantom line in FIG. 8) of washer $36_o$. Unlike the washers 36 shown in FIGS. 4 and 5, the end 49 of each of the washers shown in FIGS. 6–9 is angled at an angle other than 90° relative to the side walls of the cylindrically-shaped body 46, giving the body 46 a wedge shape. As a result of the angled end 49 of body 46, the central axis of the hole 48 through washer $36_o$ shown in FIGS. 8–9 is not parallel to the longitudinal axis of the body 46.

Like the washers 36 shown in FIGS. 4–5, the washers 36 shown in FIGS. 6–9 are provided with means for rotatably engaging the spinal stabilizer 20. As described above, in the preferred embodiment, the stabilizer engaging means takes the form of a shoulder 50 formed on the body 46 of washers $36_c$ and $36_o$ which rests on the margins of the hole 52 formed in the ends 44 of cross-bar 32 when the washer $36_c$ or $36_o$ is assembled to the cross-bar 32 (the manner in which the shoulder functions is described below). Those skilled in the art will recognize from this disclosure that other shoulder engaging means such as are described above may be provided on the washers 36 to accomplish the intended function of allowing the washer 36 to rotate in engagement with cross-bar 32.

The bodies 46 of the washers 36 are described as being cylindrical to provide a basis for referring to the longitudinal axis of the washer 36 even though it will be recognized that the height of the right angle cylinder defined by the washers of FIGS. 4 and 5 is minimal since the washers shown in FIGS. 4 and 5 are accurately described as "flat washers." However, as set out above, one end 49 of the bodies 46 of the washers 36 shown in FIGS. 6–9 is angled relative to the side walls of the cylindrically-shaped body 46 of washer 36. In the embodiments shown in FIGS. 4 and 5, the end 49 is angled at an angle of approximately 90° such that the washers shown in those figures are flat, but the end 49 of the bodies 46 of the washers 36 shown in FIGS. 6–9 is angled relative to the side walls at an angle other than 90° such that the bodies 46 of washers 36 shown in those figures have a substantial vertical dimension and are wedge-shaped rather than flat.

Referring now to FIGS. 10 and 11, an alternative embodiment of the washer of the present invention is shown. The washer 36 shown in FIGS. 11 and 12 is similar to the washers shown in FIGS. 6–9, but is provided with a concave upper surface 49 for interaction with a nut 38 (not shown) having a convex lower surface. When tightened onto the pedicle screw 34, the concave upper surface 49 provides an even greater range of angles and adjustability of placement of the screw 34 relative to the central axis of the spinal column.

As best shown in FIGS. 3 and 12, washers 36 rotatably engage cross-bar 32 at the ends 44. As described above, rotatable engagement is accomplished by resting the shoulders 50 of washers 36 comprising the preferred stabilizer engaging means on the margins of the holes 52 at the ends of cross-bars 32. During the surgical procedure, the surgeon selects either a flat washer with a longitudinal passage coincident with the center of the longitudinal axis of the washer (FIG. 4), a flat washer with a passage offset from the center of the longitudinal axis of the washer (FIG. 5), a wedge-shaped washer with a passage coincident with the center of the longitudinal axis of the washer (FIGS. 6–7), or a wedge-shaped washer with a passage offset from the center of the longitudinal axis of the washer (FIGS. 8–9), and then rotates the body 46 of the washer 36 selected in the hole 52 to provide infinite adjustability of the linkage between the cross-bar 32 and screw 34, regardless of the angle and position of the screws 34 in the pedicle 40 of each vertebrae and regardless of the shape, size, or pathology of the vertebrae and/or pedicle. The washer selected is preferably the washer which, by its shape and ability to be rotated, locates the passage therethrough in the proper position for receiving the screw 34 while maintaining an angle of approximately 90° between the longitudinal axis of the screw 34 and the surface 49 of the washer against which the nut 38 bears when tightened to effectively transfer load from the spinal column 24 to the implant 20.

To facilitate assembly of the cross-bar 32 to the screws 34, one end 44 of cross-bar 32 may be provided with a gap or break 45 through which the portion of the screw 34 protruding from the pedicle is maneuvered. Also, because the angle between the underside of cross-bar 32 and the longitudinal axis of screw 34 is unlikely to be a 90° angle and/or the screw 34 may be positioned close to the inside margin of the hole 52 in cross-bar 32, the upper surface 37 of the head 35 of screw 34 is rounded and the inside surface of the margin of the holes 52 in cross-bar 32 is beveled as shown at reference numeral 53 in FIG. 13. In another embodiment (not shown), the head of screw 34 is sized so as to contact the margin of hole 52 in cross-bar 32, the bevel 53 and complementary rounded upper surface 37 of the screw 34 helping to center the longitudinal axis of hole 52 in cross-bar 32 on the longitudinal axis of screw 34.

FIG. 12 shows the interaction and adjustability of the spinal implant of the present invention by showing one screw 34 to which a nut 38 is tightened against the wedge-shaped washer $36_o$ of FIGS. 8 and 9 with the washer 360 having been rotated relative to cross-bar 32 so that the screw 34 is angled anteriorially (with reference to the patient) while also being angled inwardly (relative to the central axis of the spinal column 24). A flat washer $36_o$ is shown on the other side of the cross-bar 32 which has been rotated so that the screw 34 is not centered in the hole 52 of cross-bar 32 but the inward angle of the screw resulting from the downward bend at the ends 44 of cross-bar 32 is maintained. Cross-bar 32 is shown with an optional nipple 56 forming a stop surface 58 near the holes 52 therethrough which acts, by engagement of the O.D. of the washer 36, to restrain any tendency of the washer 36 to move inwardly from the ends 44 of cross-bar while the nut 38 is being tightened against the washer 36 when in place in the hole 52 in cross-bar 32.

Referring briefly again to FIG. 1, the portion of cross-bar 32 intermediate the ends 44 is provided with a plurality of nested slots 60 of a type known in the art (see, for instance, U.S. Pat. No. 4,696,290 and the so-called VSP spinal fixation system described in J. W. Brantigan, et al., Posterior lumbar interbody fusion technique using the variable screw placement spinal fixation system, in D. M. Arnold and J. E. Lonstein (Eds.), 6 State of the Art Reviews—Spine: Pedicle Fixation of the Lumbar Spine 201–234 (Philadelphia: Nanley & Belfus, Inc.) 1992, both references being hereby incorporated in their entirety by this specific reference thereto) for precise placement of the screws 30 securing the rods 22 to the cross-bars 32 along the longitudinal axis of cross-bar 32. The screws 30 for securing the rods 22 to the cross-bars 32 are of the above-described type known in the art in which the portion of the screw which extends above the top surface of the nut 28 is broken off after the nut is tightened.

By comparison to FIG. 1, it can be seen that in the embodiment shown in FIG. 12, the attachment between rods 22 and cross-bars 32 is accomplished by tightening nuts 28 to the posts 62 integrally mounted to the plate 64 which moves from side to side along the longitudinal axis of cross-bar 32 in the slot 66 formed therein. The plate 64 is comprised of a flat portion (not visible in FIG. 12 because of the perspective in the figure) which extends under the cross-bar and which is tightened against the underside of cross-bar 32 when the nut 28 is tightened against a rod 22 to prevent further side to side movement of the plate 64 and post 62. Before tightening the nut 28, the plate is moved by the surgeon to the position which allows precise alignment of the rod 22 with the cross-bar 32.

In the alternative embodiment shown in FIGS. 14–15, the rods 22 are of a type known in the art such as those available from MOSS® Miami (Cat. No. 1745-70, -72, and -74) which are attached to cross-bars 32 by U-shaped connectors 68 having threads 70 formed on the outside surfaces thereof. Connectors 68 are integrally mounted to a plate 64 having a construction similar to that of the so-called axial connectors available from MOSS® Miami (Cat. No. 1745-61 and -62), e.g., two halves (not shown) with threaded posts and nuts for connecting the halves on the top and bottom of the cross-bar 32 to clamp the cross-bar 32 and prevent side to side movement of the plate 64 in the slot 66 in cross-bar 32 in which the plate 64 moves. Alternatively, the plate 64 is provided with a portion extending under cross-bar 32 which is tightened against the underside of cross-bar 32 when the nut 28 is tightened on connector 68 to resist further side to side movement. Those skilled in the art will recognize from this description of the connectors 68 and plates 64 that a similar arrangement may be used in place of the nested slots 60 in the cross-bar 32 of the embodiment shown in FIG. 1 wherein the threaded posts 62 are replaced by connectors 68 for precise lateral placement of the point at which the rods 22 are attached to cross-bars 32. In such an embodiment, connectors 68 are provided with a head for engaging the underside of the cross-bar 32 in the same manner as the screws 30.

Referring now to FIGS. 16–18, there is shown a cross-bar 72 of a type modified for use in connection with the embodiment of the spinal stabilizer of the present invention shown in FIGS. 14–15. The cross-bar 72 is provided with hooks 74 for engaging the lamina of the vertebra and a retainer 76 which is curved so as to extend under the lamina to which cross-bar 72 is to be affixed. The hooks 74 extend through a slot (not numbered for the sake of clarity) formed at approximately a right angle to the longitudinal axis of cross-bar 72 and are extended in and out of that slot until they are adjusted so as to tightly engage the posterior margin of the lamina and then set in that position by tightening the set screw 78 provided in cross-bar 72 for that purpose. U-shaped connectors 68 mounted on plates 64 as described above are provided for connecting to a rod 22 as shown in FIGS. 14–15.

Although described in terms of the presently preferred embodiment shown in the figures, those skilled in the art will recognize from this description that changes can be made to the component parts of the present invention without changing the manner in which those component parts function to achieve their intended result. For instance, the present invention is equally adaptable to a spinal fixation system which is comprised of rods on either side of the processes of the vertebrae which may or may not be connected by a cross-bar or a system comprised of a single rod down the dorsal aspect of the spinal column after removal of the dorsal processes rather than the ladder-type system shown in the figures. All such changes, and the others known to those skilled in the art, are intended to fall within the scope of the following non-limiting claims.

What is claimed is:

1. A set of washers, each washer of said set of washers comprising a cylindrical body having a passage therethrough for receiving a screw for connecting an internal spinal stabilizer to a vertebrae of a patient comprising:

a first cylindrical body having one end angled at an angle other than 90° with respect to the side walls of the cylinder, the longitudinal passage being offset from the center of the longitudinal axis of said first body;

a second cylindrical body having one end angled with respect to the side walls of the cylinder at an angle different from the angle of the end of the first cylindrical body; and means formed on each of said first and second bodies for rotatably engaging the spinal stabilizer.

2. The set of washers of claim 1 wherein the end of said second cylindrical body is angled at an angle of 90° relative to the side wall of the cylinder.

3. The set of washers of claim 2 wherein the central axis of the longitudinal passage in either said first body or said second body, or each of said first and second body, is not parallel to the longitudinal axis of said body.

4. The set of washers of claim 1 wherein said engaging means comprises a shoulder formed on each of said first and second bodies.

5. An internal spinal stabilizer comprising:

a first elongate member;

a second elongate member attached to said first elongate member and having an aperture therein;

a screw for passing through the aperture in said second elongate member and receiving a nut for affixing said second elongate member to the vertebra of a patient;

a set of washers, each of said washers having a passage therethrough for receiving said screw (a) at least one of the washers in said set of washers comprising a body having an end defining a surface against which the nut received on said screw bears that is angled at an angle of 90° relative to the side wall of the washer, (b) the central axis of the passage through at least one of the washers in said set of washers being offset from the center of the body forming the washer, and (c) at least one of the washers in said set of washers comprising a body having an end defining a surface against which the nut received on said screw bears that is angled at an angle different from the angle of the end of another washer in said set of washers; and each of said washers having means formed thereon for rotatably engaging said second elongate member adjacent the periphery of the aperture therein at any of a plurality of orientations relative to said second elongate member, each said washer being rotatable relative to said second elongate member about an axis extending through the aperture in said second elongate member when engaged thereto, the nut received on said screw bearing against one washer selected from said set of washers for providing a multiaxial coupling between the vertebra and said second elongate member when engaging said second elongate member and rotated relative to said elongate member to transfer load from the vertebrae of the patient to said second elongate member regardless of the angle and/or position of said screw relative to said second elongate member.

6. The spinal stabilizer of claim 5 therein the angle of the surface against which the nut received on said screw bears of at least one washer of said set of washers is an angle of 90° relative to the side wall of the washer.

7. The spinal stabilizer of claim 5 wherein at least one washer of said set of washers is provided with a surface against which said screw bears that is angled relative to the axis of the passage through the washer and a passage with a central axis that is coincident with the center axis of the washer.

8. The spinal stabilizer of claim 5 wherein said second elongate member is attached to said first elongate member at approximately a 90° angle.

9. The spinal stabilizer of claim 5 wherein said second elongate member is slidably attached to said first elongate member for movement relative to said first elongate member.

10. The spinal stabilizer of claim 5 wherein said rotatable engagement means comprises a shoulder formed on the washers comprising said set of washers for resting on said second elongate member adjacent the periphery of the aperture therethrough.

* * * * *